United States Patent
Jung et al.

(10) Patent No.: US 12,295,701 B2
(45) Date of Patent: May 13, 2025

(54) APPARATUS AND METHOD FOR ESTIMATING BIO-INFORMATION

(71) Applicant: SAMSUNG ELECTRONICS CO., LTD., Suwon-si (KR)

(72) Inventors: Myoung Hoon Jung, Suwon-si (KR); Kun Sun Eom, Suwon-si (KR); Jin Young Park, Suwon-si (KR); Yoon Jae Kim, Suwon-si (KR); Hyun Seok Moon, Suwon-si (KR); Jeong Eun Hwang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 129 days.

(21) Appl. No.: 18/107,166

(22) Filed: Feb. 8, 2023

(65) Prior Publication Data
US 2024/0090771 A1    Mar. 21, 2024

(30) Foreign Application Priority Data
Sep. 16, 2022    (KR) .................. 10-2022-0116734

(51) Int. Cl.
*A61B 5/00*    (2006.01)

(52) U.S. Cl.
CPC ............ *A61B 5/0082* (2013.01); *A61B 5/742* (2013.01)

(58) Field of Classification Search
CPC .............................. A61B 5/0082; A61B 5/742
See application file for complete search history.

(56) References Cited

U.S. PATENT DOCUMENTS

| | | | |
|---|---|---|---|
| 8,260,402 B2 | 9/2012 | Ermakov et al. | |
| 8,460,537 B2 | 6/2013 | Blythe et al. | |
| 8,623,198 B2 | 1/2014 | Chatelier et al. | |
| 9,943,256 B2 | 4/2018 | Varsavsky et al. | |
| 10,416,079 B2 | 9/2019 | Magnussen et al. | |
| 10,416,110 B2 | 9/2019 | Wu | |
| 11,085,876 B2 | 8/2021 | Magnussen et al. | |
| 2010/0016689 A1* | 1/2010 | Kanayama | A61B 5/1455 600/316 |
| 2011/0139634 A1 | 6/2011 | Chou et al. | |
| 2020/0029873 A1* | 1/2020 | Park | A61B 5/486 |
| 2020/0060585 A1* | 2/2020 | Harris | A61B 5/6824 |
| 2020/0196935 A1* | 6/2020 | Eom | A61B 5/443 |

(Continued)

FOREIGN PATENT DOCUMENTS

| KR | 10-2239896 B1 | 4/2021 |
|---|---|---|
| KR | 10-2022-0041750 A | 4/2022 |
| KR | 10-2022-0053450 A | 4/2022 |

*Primary Examiner* — Sean A Frith
(74) *Attorney, Agent, or Firm* — Sughrue Mion, PLLC

(57) ABSTRACT

An apparatus for estimating bio-information includes: a sensor including one or more light sources configured to emit light to an object and a plurality of detectors configured to detect light reflected from the object; and a processor configured to transform a plurality of light quantities obtained from respective detectors of the plurality of detectors to a distance domain, to combine the plurality of transformed light quantities in the distance domain, to correct the combined light quantity based on a reference light quantity for correcting a deviation of a distance between the one or more light sources and the plurality of detectors, and to estimate bio-information based on a light quantity resulting from the correction.

10 Claims, 10 Drawing Sheets

(56) References Cited

U.S. PATENT DOCUMENTS

| | | |
|---|---|---|
| 2020/0352478 A1 | 11/2020 | Park |
| 2021/0052221 A1* | 2/2021 | Panneer Selvam ... A61B 5/1117 |
| 2021/0076958 A1* | 3/2021 | Pierro .................. A61B 5/6815 |
| 2021/0093237 A1* | 4/2021 | Venugopal .............. H01L 31/16 |
| 2021/0113121 A1* | 4/2021 | Diab .................... A61B 5/0073 |
| 2022/0099565 A1 | 3/2022 | Moon et al. |
| 2022/0125321 A1 | 4/2022 | Ko et al. |

* cited by examiner

APPARATUS AND METHOD FOR ESTIMATING BIO-INFORMATION

CROSS-REFERENCE TO RELATED APPLICATION(S)

This application claims priority from Korean Patent Application No. 10-2022-0116734, filed on Sep. 16, 2022, in the Korean Intellectual Property Office, the entire disclosure of which is incorporated herein by reference for all purposes.

BACKGROUND

1. Field

Apparatus and methods consistent with this disclosure relate to technology for estimating bio-information, and more particularly to technology for non-invasively estimating antioxidant levels.

2. Description of Related Art

Reactive oxygen species act as an important biological defense factor such as white blood cells protecting the body against infections. However, it has been known that excessive generation of reactive oxygen species in the body may lead to various tissue diseases. Common factors that cause the reactive oxygen species include stress, alcohol, peroxides, medicine, and the like. The reactive oxygen species produced by these factors may cause cranial nerve diseases, circulatory diseases, cancer, digestive tract diseases, liver diseases, arteriosclerosis, renal diseases, diabetes, aging, and the like. Our bodies have a series of antioxidant defense systems to protect against oxygen toxicity. For normal operation of the systems, it is essential to consume sufficient antioxidants such as vitamin E, vitamin C, carotenoid, flavonoid, and the like. It is important to eat as many foods that are rich in antioxidants as possible for an effective antioxidant action. Accordingly, there is a need for an apparatus for easily identifying the amount of antioxidant components in the body.

SUMMARY

According to an embodiment, an apparatus for estimating bio-information, the apparatus may include: a sensor including one or more light sources configured to emit light to an object and a plurality of detectors configured to detect light reflected from the object; and a processor configured to transform a plurality of light quantities obtained from respective detectors of the plurality of detectors to a distance domain, the processor is further configured to combine the plurality of transformed light quantities in the distance domain into a combined light quantity, to correct the combined light quantity based on a reference light quantity, wherein the reference light quantity corrects for a deviation of a distance between the one or more light sources and the plurality of detectors to provide a corrected light quantity, and to estimate bio-information based on the corrected light quantity.

According to an embodiment, the processor may transform the plurality of light quantities to the distance domain by applying a logarithmic operation to each of the plurality of light quantities.

According to an embodiment, the processor may combine the plurality of transformed light quantities using at least one of an arithmetic mean, a harmonic mean, and a geometric mean in the distance domain.

According to an embodiment, the processor may correct the combined light quantity based on a difference between the reference light quantity and the combined light quantity.

According to an embodiment, the processor may be further configured to drive the one or more light sources to emit light to a standard material, to obtain a plurality of standard light quantities from respective detectors of the plurality of detectors, to transform the plurality of standard light quantities to the distance domain, and to generate the reference light quantity by combining the plurality of transformed standard light quantities in the distance domain.

According to an embodiment, the processor may be further configured to calculate absorbance based on the corrected light quantity to obtain a feature value, and estimates the bio-information based on the obtained feature value.

According to an embodiment, the processor may be further configured to drive the one or more light sources at a plurality of wavelengths and the plurality of light quantities obtained from the plurality of detectors include different wavelengths corresponding to the plurality of wavelengths, wherein the processor determines a corrected light quantity for each of the different wavelengths, and calculating the absorbance includes calculating a plurality of absorbance values from the corrected light quantity for each of the different wavelengths, and the processor is further configured to obtain an antioxidant peak by combining the plurality of calculated absorbance values using a predefined antioxidant level estimation model to obtain an antioxidant level.

According to an embodiment, the one or more light sources may have a wavelength range of 400 nm to 600 nm.

According to an embodiment, the processor may simultaneously may drive all or some of the one or more light sources or sequentially drives the one or more light sources according to wavelength.

According to an embodiment, the plurality of detectors may be at least four in number.

According to an embodiment, a method of estimating bio-information, the method may include: using one or more light sources to emit light to an object; using a plurality of detectors to detect light reflected from the object; using a processor to: transform a plurality of light quantities obtained from respective detectors of the plurality of detectors to a distance domain; combine the transformed plurality of light quantities in the distance domain to provide a combined light quantity; correct the combined light quantity based on a reference light quantity, wherein the reference light quantity corrects for a deviation of a distance between the one or more light sources and the plurality of detectors; and estimate bio-information based on the corrected light quantity.

According to an embodiment, the transforming the plurality of light quantities to the distance domain may include using the processor to apply a logarithmic operation to each of the plurality of light quantities.

According to an embodiment, the combining the plurality of the transformed light quantities in the distance domain may include determining at least one of an arithmetic mean, a harmonic mean, and a geometric mean.

According to an embodiment, the correcting of the combined light quantity may include correcting the combined light quantity based on a difference between the reference light quantity and the combined light quantity.

According to an embodiment, the estimating of the bio-information may include calculating absorbance based on the corrected light quantity, obtaining a feature value based on the calculated absorbance, and estimating the bio-information based on the obtained feature value.

According to an embodiment, the method may further include: using the processor to drive the one or more light sources at a plurality of wavelengths and the plurality of light quantities obtained from the plurality of detectors include different wavelengths corresponding to the plurality of wavelengths, wherein the processor determines corrected light quantity for each of the different wavelengths, and calculating the absorbance includes calculating a plurality of absorbance values from the corrected light quantity for each of the different wavelengths, and the processor may be further configured to obtain an antioxidant peak by combining the plurality of calculated absorbance values, using a predefined antioxidant level estimation model.

According to an embodiment, an electronic device may include: a main body; a sensor including one or more light sources and a plurality of detectors which are disposed on a first surface of the main body; a display device disposed on a second surface of the main body; and a processor configured to drive the one or more light sources, to transform a plurality of light quantities obtained from respective detectors of the plurality of detectors to a distance domain, to combine the plurality of transformed light quantities in the distance domain to provide a combined light quantity, to correct the combined light quantity based on a reference light quantity to provide a corrected light quantity, the reference light quantity correcting for a deviation of a distance between the one or more light sources and the plurality of detectors, and to estimate bio-information based on the corrected light quantity.

According to an embodiment, the processor may transform the plurality of light quantities to the distance domain by applying a logarithmic operation to each of the plurality of light quantities.

According to an embodiment, during estimation of the bio-information, the processor may output a text message for guiding a user to estimate the bio-information, and upon completing the estimation of the bio-information, the processor outputs an estimation result to the display device.

According to an embodiment, an electronic device may include: one or more first light sources configured to emit first light to an object; one or more second light sources configured to emit second light to the object; a plurality of detectors configured to detect the first light, emitted by the first light sources and reflected or scattered from the object, and the second light emitted by the second light sources and reflected or scattered from the object; and a processor configured to estimate first bio-information based on the first light detected by the plurality of detectors, and second bio-information based on the second light detected by the plurality of detectors, wherein the processor drives the first light sources and the second light sources and the processor transforms a plurality of light quantities obtained from respective detectors of the plurality of detectors for the respective light sources to a distance domain, combines the plurality of transformed light quantities in the distance domain to provide a combined light quantity, corrects the combined light quantity based on a reference light quantity, wherein the reference light quantity corrects for a deviation of a distance between the first light sources and the plurality of detectors to provide a corrected light quantity, and the processor estimates the first bio-information based on the corrected light quantity.

Figure 1:
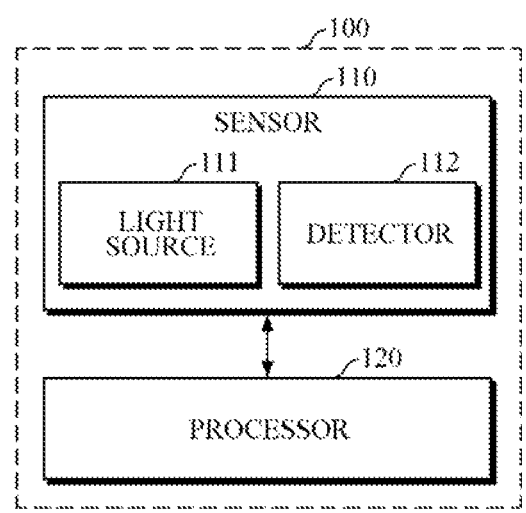
FIG. 1 is a block diagram illustrating an apparatus for estimating bio-information according to an embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Details of example embodiments are included in the following detailed description and drawings. Advantages and features example embodiments, and a method of achieving the same will be more clearly understood from the following description with reference to the accompanying drawings.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'unit' or 'module', etc., should be understood as a unit that performs at least one function or operation and that may be embodied as hardware (e.g. a processor), software, or a combination thereof.

FIG. 1 is a block diagram illustrating an apparatus for estimating bio-information according to an embodiment.

Referring to FIG. 1, an apparatus 100 for estimating bio-information includes a sensor 110 and a processor 120. The sensor 110 may include a light source 111 for emitting light to an object and a detector 112 for detecting light reflected from the object.

The light source 111 may include a light emitting diode (LED), a laser diode, a phosphor, and the like. There may be one or more light sources 111, each of which may emit light of different wavelengths (e.g., red, green, blue, and infrared wavelengths, etc.). For example, a measurable wavelength range may be from 400 nm to 600 nm. The detector 112 may include a photodiode, a phototransistor (PTr), a Complementary Metal Oxide Semiconductor (CMOS) image sensor, a charge-coupled device (CCD) image sensor, etc., and may be formed as a plurality of detectors or a detector array. In order to have a plurality of optical paths between light sources and detectors, the plurality of detectors may be at least four in number. The plurality of detectors or the detector array may be formed in a predetermined shape. As one example, the detectors or detector array may be arranged in a circle around the light sources 111 at a periphery thereof, or in various shapes, such as a square, a triangle, and the like.

Figure 2A:
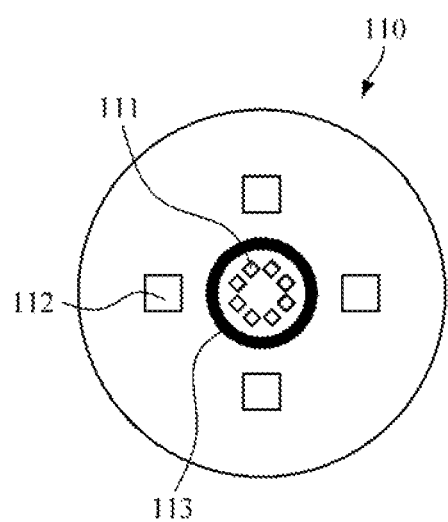
FIGS. 2A and 2B are diagrams illustrating arrangement of light sources and detectors according to an embodiment.
Figure 2B:
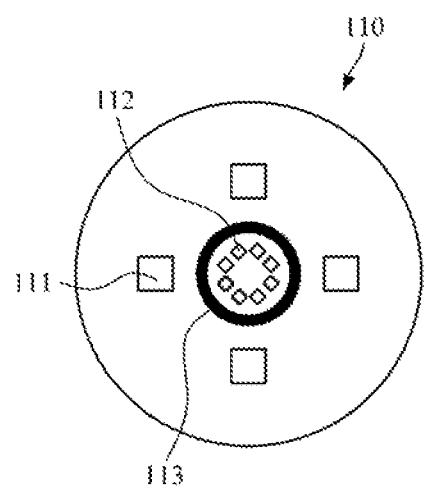

FIGS. 2A and 2B are diagrams illustrating arrangement of the light sources 111 and the detectors 112 according to an embodiment of the present disclosure.

Referring to FIG. 2A, the one or more light sources 111 may be disposed inside a wall 113, and the plurality of detectors 112 may be disposed outside the wall 113. In addition, referring to FIG. 2B, the plurality of detectors 112 may be disposed inside the wall 113, and the one or more light sources 111 may be disposed outside the wall 113. In this case, the one or more light sources 111 or the plurality of detectors 112, which may be disposed inside the wall 113, may be disposed in an eccentric or concentric arrangement. However, the arrangement of the light sources 111 and the detectors 112 is not limited thereto. In addition, the wall 113 that separates the light sources 111 and the detectors 112 may have various shapes, including not only an annular shape but also a triangular shape, a tetragonal shape, etc., and may be omitted depending on a form factor of the sensor 110.

The processor 120 may be electrically or wirelessly connected to the sensor 110 to control the sensor 110, and may estimate bio-information by using data obtained from the sensor 110. In this case, the bio-information may be antioxidant levels indicating a concentration of an antioxidant substance. The bio-information may indicate a concentration of carotenoid accumulated in the skin. However, this is merely an example, and the bio-information may include a variety of information including blood glucose, triglyceride, alcohol, lactate, skin pigment, bloodstream amount, and the like. Further, the processor 120 may also estimate bio-information using pulse wave signals (e.g., Photoplethymogram (PPG) signal), e.g., blood pressure, heart rate, vascular age, arterial stiffness, aortic pressure waveform, vascular compliance, stress index, fatigue level, skin elasticity, skin age, and the like. However, the bio-information which may be estimated is not limited thereto. For convenience of explanation, the following description will be given using an antioxidant level as an example.

First, the processor 120 may drive the one or more light sources 111 and may transform a plurality of light quantities, obtained by the plurality of detectors 112 for the respective light sources, to a distance domain. In this case, the processor 120 may simultaneously drive all or some of the one or more light sources 111 or may sequentially drive the one or more light sources 111 in predetermined time increments and may drive the light sources 111 having one or more wavelengths. A method or sequence of driving the light sources 111 is not limited thereto.

For example, by applying a logarithmic operation to each of the plurality of light quantities obtained by the detectors 112, the processor 120 may transform the plurality of light quantities to the distance domain.

Figure 3:
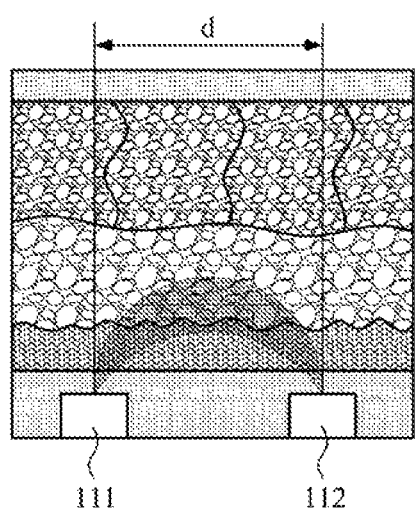
FIG. 3 is a diagram explaining an example of transforming light quantities to a distance domain.

FIG. 3 is a diagram explaining an example of transforming light quantities to a distance domain.

Referring to FIG. 3, when light emanating from the light source 111 is scattered or reflected from an object to reach the detector 112, light quantities measured by the detector 112 may be represented by the following Equation 1 according to Lambert-Beer's law.

$$I = I_0 10^{-\varepsilon cd}$$ [Equation 1]

Herein, I denotes a quantity of light incident on the detector, $I_0$ denotes a quantity of outgoing light emitted from the light source, $\varepsilon$ denotes absorbance of an antioxidant component, c denotes the concentration of the antioxidant component, and d denotes a distance between the light source and the detector.

In order to extract distance information from the light quantity I obtained by the detector 112, a logarithmic operation may be applied to Equation 1 to transform a linear domain to a distance domain. The information in the distance domain may be represented by the following Equation 2. In this case, when the logarithmic operation is applied, the base number of the logarithm may be a natural constant e, but is not limited thereto. In addition, depending on the characteristics of a manufactured sensor, a nonlinear function or an empirical equation may be used instead of the logarithmic operation, but the logarithmic operation is not limited thereto.

$$\log I = \log I_0^{-\varepsilon cd}$$ [Equation 2]

Then, the processor 120 may combine the transformed light quantities in the distance domain, which may be represented by the following Equation 3.

$$I_{fm} = f(\log I_{m1}, \log I_{m2}, \log I_{m3}, \log I_{m4})$$ [Equation 3]

For example, in the case where the sensor 110 includes one light source 111 and four detectors 112, $\log I_{m1}$ denotes a value obtained by transforming a light quantity, obtained by a first detector at a predetermined wavelength, to the distance domain, $\log I_{m2}$ denotes a value obtained by transforming a light quantity, obtained by a second detector at a predetermined wavelength, to the distance domain, $\log I_{m3}$ denotes a value obtained by transforming a light quantity, obtained by a third detector at a predetermined wavelength, to the distance domain, $\log I_{m4}$ denotes a value obtained by transforming a light quantity, obtained by a fourth detector at a predetermined wavelength, to the distance domain, and $I_{fm}$ denotes a mean value of $\log I_{m1}$, $\log I_{m2}$, $\log I_{m3}$, and $\log I_{m4}$.

In this case, the processor 120 may combine the transformed light quantities in the distance domain by using at least one of an arithmetic mean, a harmonic mean, and a geometric mean, which may be represented by the following Equations 4, 5, and 6, respectively.

$$I_{fm} = \frac{\log I_{m1} + \log I_{m2} + \log I_{m3} + \log I_{m4}}{4}$$ [Equation 4]

$$I_{fm} = \frac{4(\log I_{m1} \times \log I_{m2} \times \log I_{m3} \times \log I_{m4})}{\log I_{m1} + \log I_{m2} + \log I_{m3} + \log I_{m4} 4}$$ [Equation 5]

$$I_{fm} = \sqrt[4]{\log I_{m1} \times \log I_{m2} \times \log I_{m3} \times \log I_{m4}}$$ [Equation 6]

For example, in order to calculate the arithmetic mean, the harmonic mean, or the geometric mean, the processor 120 may preprocess a received signal by using an arithmetic mean filter, a harmonic mean filter, or a geometric mean filter. However, the method of preprocessing by the processor 120 is not limited thereto.

Then, the processor 120 may correct the combined light quantity based on a reference light quantity for correcting the deviation of a distance between the one or more light sources and the plurality of detectors. For example, the processor 120 may correct the combined light quantity based on a difference between the reference light quantity and the combined light quantity, which may be represented by the following Equation 7.

$$I_{fm}' = I_{f0} - I_{fm}$$ [Equation 7]

Herein, I denotes the reference light quantity, $I_{fm}$ denotes a mean value of the light quantities transformed to the distance domain, and $I_{fm}'$ denotes corrected $I_{fm}$ which is corrected based on the reference light quantity.

The processor 120 may drive the one or more light sources for a standard object, may transform a plurality of standard light quantities, obtained by the plurality of detectors for each of the respective light sources, to the distance domain, and may generate the reference light quantity $I_{f0}$ by combining the transformed standard light quantities in the distance domain. In this case, in order to transform the light quantities into the distance domain, the processor 120 may apply a logarithmic operation to each of the plurality of standard light quantities, and may combine the transformed standard light quantities in the distance domain by using at least one of the arithmetic mean, the harmonic mean, and the geometric mean.

In this case, the standard object may be a reflector for reflecting light (e.g., reflection mirror with 100 percent reflection, white reflector, etc.) or an object coated with a reflection material. The reflection material may be a diffuse reflection material having a reflectivity of 1% to 99%, and may be, for example, Barium sulfate (BaSO4), Teflon (PTFE), etc., but is not limited thereto.

Then, the processor 120 may estimate bio-information based on a light quantity resulting from the correction. For example, the processor 120 may calculate absorbance based on the light quantity resulting from the correction, may obtain a feature value based on the calculated absorbance, and may estimate bio-information based on the obtained feature value.

First, the processor 120 may calculate absorbance $A(\lambda)$ by applying a logarithmic operation to a difference between the reference light quantity and the combined light quantity, which may be represented by the following Equation 8. In this case, the absorbance may be calculated for each wavelength by driving the light source 111.

$$A(\lambda) = -\log \frac{I_{fm}}{I_{f0}}$$ [Equation 8]

Then, the processor 120 may obtain an antioxidant peak by combining the calculated absorbances, which may be represented by the following Equations 9 and 10.

$$AO = A_{\lambda_2} - \left(\frac{\lambda_3 - \lambda_2}{\lambda_3 - \lambda_1}\right) \times A_{\lambda_1} - \left(\frac{\lambda_2 - \lambda_1}{\lambda_3 - \lambda_1}\right) \times A_{\lambda_3}$$ [Equaiton 9]

Herein, AO denotes an example of the feature value and indicates the antioxidant peak obtained by combining the absorbances at each wavelength, $\lambda_1$, $\lambda_2$, and $\lambda_3$ denote wavelengths, and $A_{\lambda_1}$, $A_{\lambda_2}$, and $A_{\lambda_3}$ denote absorbances obtained at each wavelength by using Equation 8, in which the wavelengths become longer in the order of $\lambda_1$, $\lambda_2$, and $\lambda_3$.

In addition, Equation 10 shows an example of obtaining the antioxidant peak AO by using absorbances at four wavelengths $\lambda_1$, $\lambda_2$, $\lambda_3$, and $\lambda_4$.

$$AO = aA_{\lambda_1} + bA_{\lambda_2} + cA_{\lambda_3} + dA_{\lambda_4} + e$$ [Equation 10]

Herein, $A_{\lambda_1}$, $A_{\lambda_2}$, $A_{\lambda_3}$, and $A_{\lambda_4}$ denote absorbances obtained at each respective wavelength by using Equation 8, a, b, c, and d may be predetermined coefficients, and e may be a predetermined constant.

Then, the processor 120 may obtain an antioxidant level based on the obtained antioxidant peak AO by using a predefined antioxidant level estimation model, which may be represented by the following Equation 11.

$$Y = a \times AO + b$$ [Equation 11]

Herein, Y denotes the antioxidant level, and a and b denote predetermined values. While Equation 11 denotes an antioxidant level estimation model which is defined as a linear function, the equation is not limited thereto and may also be defined as a nonlinear function, such as a logarithmic function, an exponential function, and the like.

For example, the processor 120 may obtain the antioxidant peak, obtained using Equation 9 or Equation 10, as a final antioxidant level. In addition, the processor 120 may also obtain the final antioxidant level by transforming one more time the antioxidant peak, obtained by Equation 9 or Equation 10, by using the antioxidant level estimation model in Equation 11. However, a method of obtaining the antioxidant level is not limited thereto.

Generally, during a manufacturing process of sensors for estimating bio-information, a change in length of an optical path between the light source and the detector may occur in each of the manufactured sensors due to an arrangement deviation of devices (e.g., light source, detector, etc.). The change in optical path length may lead to a change in intensity of a measured signal, thereby reducing the accuracy of bio-information estimation. According to the embodiment, however, by transforming a plurality of light quantities, obtained by the detector, to distance information and by averaging the distance information, the effect of the arrangement deviation of the devices may be offset, thereby improving the accuracy of bio-information estimation.

Figure 4:
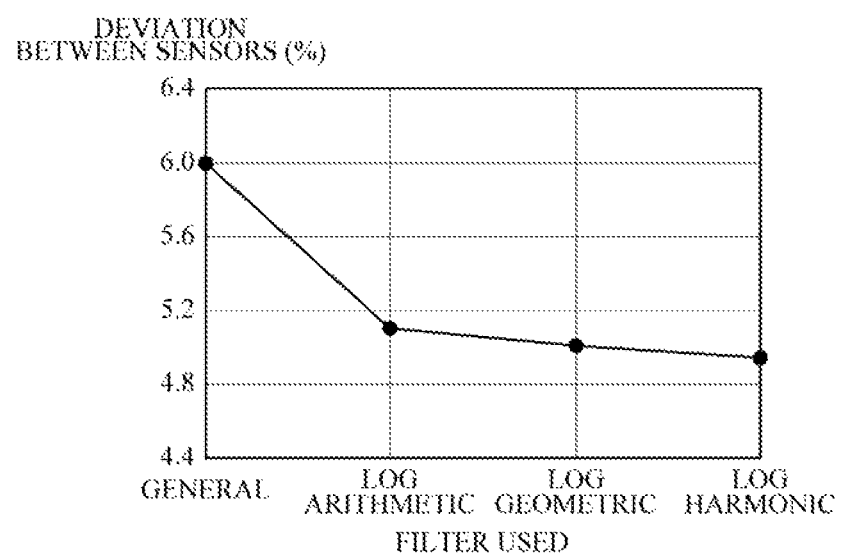
FIG. 4 is a diagram illustrating a graph showing deviation results as a percentage between sensors for cases in which distance information is averaged and a case in which distance information is not averaged.

FIG. 4 is a diagram illustrating a graph showing deviation results as a percentage between sensors for cases in which distance information is averaged and a case in which distance information is not averaged. In the graph, the X axis shows a general case in which the distance information is not averaged (general), and three cases using filtering. The filtering label on the X-axis correspond to filtering by an arithmetic mean where the distance information is calculated (log arithmetic), a geometric mean where the distance information is calculated (log geometric), and a harmonic mean where the distance information is calculated (log harmonic). The Y axis represents the percentage of deviation between sensors when a corresponding type of filtering is applied, and when no filtering is applied.

Referring to FIG. 4, it can be seen that when a plurality of light quantities, obtained by the detectors for a plurality of sensors, are transformed to distance information by applying a logarithmic function to the light quantities, and bio-information is measured by calculating the arithmetic mean, the geometric mean, and the harmonic mean of the transformed distance information, the deviation result (as a percentage) between the sensors is maintained constant and has a lower value than the deviation result between sensors in the general case where the distance information is not averaged.

Figure 5:
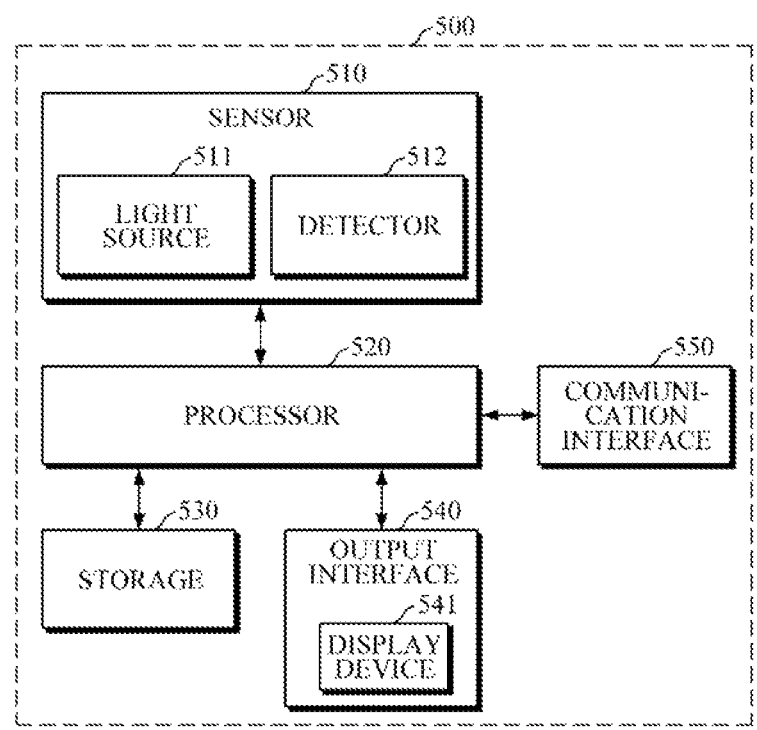
FIG. 5 is a block diagram illustrating an apparatus for estimating bio-information according to another embodiment.

FIG. 5 is a block diagram illustrating an apparatus for estimating bio-information according to another embodiment of the present disclosure.

Referring to FIG. 5, an apparatus 500 for estimating bio-information includes a sensor 510, a processor 520, a storage 530, an output interface 540, and a communication interface 550. In this case, the output interface 540 may include a display device 541. The sensor 510 and the processor 520 may be the same as the sensor 110 and the processor 120 of FIG. 1, such that a detailed description thereof will be omitted.

The storage 530 may store information related to estimating bio-information. For example, the storage 530 may store operating conditions required for operating the sensor 510, and various other data required for components of the apparatus. The various data may include, for example, input data and/or output data for software and instructions associated with the software, and the like. For example, the storage 530 may store various data including the reference light quantity, the estimated bio-information value, the bio-information estimation model, and/or user characteristic information, such as a user's age, gender, health condition, and the like.

The storage 530 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The output interface 540 may provide processing results of the processor 520 for a user. For example, the output interface 540 may display an estimation result (e.g., antioxidant level), obtained when estimation is completed by the processor 520, on the display device 541. For example, by dividing a display area into two or more areas, the output interface 540 may output absorbance information used for estimating bio-information in a first area, and may output a bio-information estimation result in a second area. Further, the output interface 540 may output bio-information estimation history data over a predetermined period of time in graph form in the first area; and when a user selects any one point in time in a graph, the output interface 540 may output a bio-information estimation result at the selected time point in the second area. In this case, if an estimated antioxidant value falls outside a normal range, the output interface 540 may provide warning information for a user by changing color, line thickness, etc., or displaying the abnormal value along with the normal range, so that the user may easily recognize the abnormal value. Further, along with or without the visual output, the output interface 540 may provide the user with the bio-information estimation result using a non-visual method by voice, vibrations, tactile sensation, and the like through an audio output module such as a speaker, or a haptic module and the like.

In addition, during estimation of bio-information, the output interface 540 may output a text message for guiding a user to estimate bio-information to the display device 541. For example, the processor 520 may determine a bio-information measurement state, and if the state is before measurement of bio-information is performed, the processor 130 may display information for recommending estimation of bio-information on the display device 541. For example, the processor 520 may output a text message, such as "would you like to measure your antioxidant level?", on the display device 541. However, the recommendation text message is not limited thereto.

The communication interface 550 may communicate with an external device to transmit and receive various data related to estimating bio-information. The external device may include an information processing device such as a smartphone, a tablet PC, a desktop computer, a laptop computer, and the like. For example, the communication interface 550 may transmit a bio-information estimation result to a user's smartphone and the like, so that the user may manage and monitor a substance analysis result by using a device having relatively high performance.

The communication interface 550 may communicate with the external device by using communication techniques, such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G, 4G, 5G, and 6G communications, and the like. However, this is merely exemplary and is not intended to be limiting.

Figure 6:
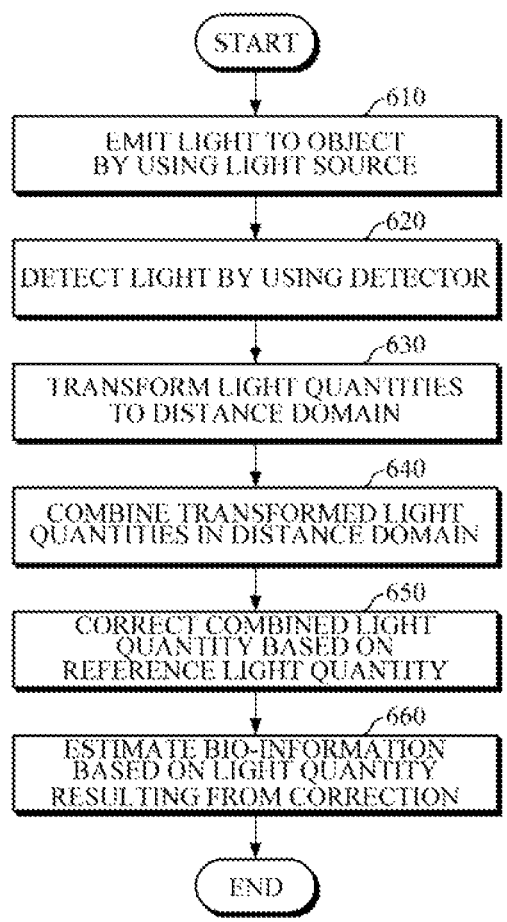
FIG. 6 is a flowchart illustrating a method of estimating bio-information according to an embodiment.

FIG. 6 is a flowchart illustrating a method of estimating bio-information according to an embodiment of the present disclosure.

The method of FIG. 6 is an example of a method of estimating bio-information which is performed by the apparatuses 100 and 500 for estimating bio-information of FIGS. 1 and 5, and will be briefly described below in order to avoid redundancy.

First, the apparatus for estimating bio-information may emit light to an object by using one or more light sources in 610 and may detect light reflected from the object by using a plurality of detectors in 620. In this case, the one or more light sources may emit light in a wavelength range of 400 nm to 600 nm, and the plurality of detectors may be at least four in number.

Then, the apparatus for estimating bio-information may transform a plurality of light quantities, obtained by the plurality of detectors, to a distance domain in 630. In this case, by applying a logarithmic operation to each of the plurality of light quantities, the apparatus for estimating bio-information may transform the light quantities to the distance domain.

Subsequently, the apparatus for estimating bio-information may combine the transformed light quantities in the distance domain in 640. For example, the apparatus for estimating bio-information may combine the transformed light quantities in the distance domain by using at least one of an arithmetic mean, a harmonic mean, and a geometric mean.

Next, the apparatus for estimating bio-information may correct the combined light quantity based on a reference light quantity for correcting the deviation of a distance between the one or more light sources and the plurality of detectors in 650. For example, the apparatus for estimating bio-information may correct the combined light quantity based on a difference between the reference light quantity and the combined light quantity. In this case, the apparatus for estimating bio-information may drive one or more light sources for a standard object, may transform a plurality of standard light quantities, obtained by the plurality of detectors for the respective light sources, to a distance domain, and may generate the reference light quantity by combining the transformed standard light quantities in the distance domain.

Then, the apparatus for estimating bio-information may estimate bio-information based on a light quantity resulting from the correction in 660. In this case, the apparatus for estimating bio-information may calculate absorbances based on the light quantity resulting from the correction, may obtain a feature value based on the calculated absorbance, and may estimate bio-information based on the obtained feature value. For example, the apparatus for estimating bio-information may obtain an antioxidant peak by combining the calculated absorbances and may obtain an antioxidant level based on the obtained antioxidant peak by using a predefined antioxidant level estimation model.

Figure 7:
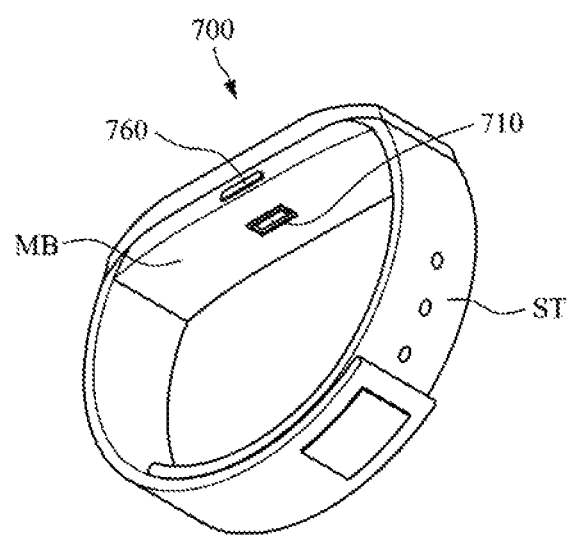
FIGS. 7 to 9 are diagrams illustrating examples of structures of an electronic device.
Figure 8:
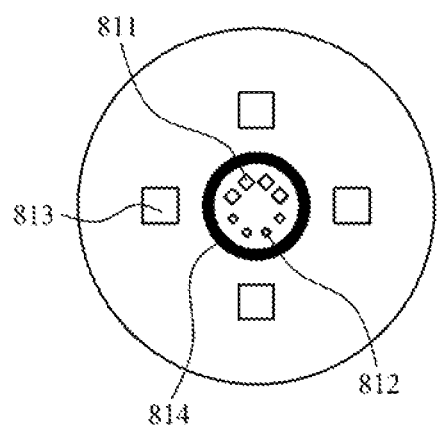
Figure 9:
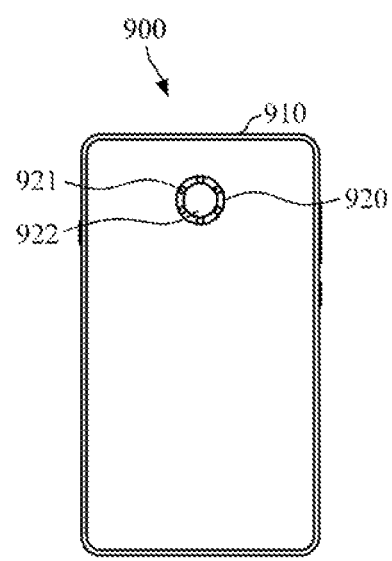

FIGS. 7 to 9 are diagrams illustrating examples of structures of an electronic device.

Referring to FIG. 7, the electronic device may be implemented as a smart watch wearable device 700 including a main body MB and a wrist strap ST.

The main body MB may be formed in various shapes. A battery may be embedded in the main body MB and/or the strap ST to supply power to various components of the wearable device. The strap ST may be connected to both ends of the main body to allow the main body to be worn on a user's wrist, and may be flexible so as to be wrapped around the user's wrist. The strap ST may be composed of a first strap and a second strap which are separated from each other. One ends of the first strap and the second strap are connected to both sides of the main body MB, and the other ends thereof may be connected to each other via a fastening means. In this case, the fastening means may be formed as magnetic fastening, Velcro fastening, pin fastening, and the like, but is not limited thereto. Further, the strap ST is not limited thereto, and may be integrally formed as a non-detachable band.

The main body MB may include a sensor 710 including one or more light sources and detectors which are disposed on a first surface of the main body, a processor, a display device disposed on a second surface of the main body, a storage, and a communication interface. However, depending on the size and shape of a form factor and the like, some of the storage and the communication interface may be omitted.

The processor mounted in the main body MB may be electrically connected to various components, including the sensor 710. The processor may drive the one or more light sources 111 and may transform a plurality of light quantities, obtained by the plurality of detectors for the respective light sources, to a distance domain, may combine the transformed light quantities in the distance domain, may correct the combined light quantity based on a reference light quantity for correcting the deviation of a difference between the one or more light sources and the plurality of detectors, and may estimate bio-information based on a light quantity resulting from the correction. In this case, by applying a logarithmic operation to each of the plurality of light quantities, the apparatus for estimating bio-information may transform the light quantities to the distance domain.

A manipulator 760 may be formed on a side surface of the main body MB, as illustrated herein. The manipulator 760 may receive a user's command and may transmit the received command to the processor. In addition, the manipulator 760 may have a power button to turn on/off the wearable device 700.

A display device (e.g., display) may be provided on a front surface of the main body MB and may display various application screens, including bio-information, time information, received message information, and the like. For example, during estimation of bio-information, the processor may output a text message for guiding a user to estimate bio-information, and when estimation of bio-information is complete, the display device may output an estimation result to the display device.

According to an embodiment of the present disclosure, the light sources and the detectors of the sensor 710 of the electronic device may be disposed to measure a plurality of bio-information items.

FIG. 8 is a diagram illustrating an example of light sources and detectors which are disposed to measure a plurality of bio-information items.

Referring to FIG. 8, the sensor may include: first light sources 811 for emitting first light to an object; second light sources 812 for emitting second light to the object; a plurality of detectors 813 for detecting the first light, emitted by the first light sources and reflected or scattered from the object, and the second light emitted by the second light sources and reflected or scattered from the object; and a wall 814 for separating the light sources 811 and 812 and the detectors 813.

The processor may estimate first bio-information based on the first light detected by the plurality of detectors and may estimate second bio-information based on the second light detected by the plurality of detectors. For example, the first light and the first bio-information may be an antioxidant signal and an antioxidant level, and the second light and the second bio-information may be a pulse wave signal and blood pressure. In this case, the processor may simultaneously or separately measure the first bio-information and the second bio-information.

For example, the processor may drive the first light sources to transform a plurality of light quantities, obtained by the plurality of detectors for the respective light sources, to a distance domain, may combine the transformed light quantities in the distance domain, may correct the combined light quantity based on a reference light quantity for correcting the deviation of a distance between the first light sources and the plurality of detectors, and may estimate the first bio-information based on the light quantity resulting from the correction. In addition, the processor may drive the second light sources to extract a feature value from a signal, having a highest intensity among the pulse wave signals acquired by the plurality of detectors, and may estimate the second bio-information based on the feature value. However, the method of estimating the first bio-information and the second bio-information by the processor is not limited thereto.

FIG. 9 is a diagram illustrating an example of a smart device. In this case, the smart device may include a smartphone, a tablet PC, and the like. The smart device may include various embodiments of the aforementioned apparatuses 100 and 500 for estimating bio-information.

Referring to FIG. 9, a smart device 900 may include a main body 910 and a sensor 920 mounted on one surface of the main body 910. For example, the sensor 920 may include one or more light sources 922 disposed at the center thereof, and a plurality of detectors 921 arranged at the periphery thereof. A configuration of the sensor 920 is described in detail above, such that a description thereof will be omitted.

In addition, a display may be mounted on a front surface of the main body 910. The display may visually output a bio-information estimation result and the like. The display may include a touch screen, and may receive information input through the touch screen and transmit the information to the processor.

As described above, the processor may transform a plurality of light quantities, obtained by the plurality of detectors for the respective light sources, to a distance domain, may combine the transformed light quantities in the distance domain, may correct the combined light quantity based on a reference light quantity for correcting the deviation of a distance between the one or more light sources and the plurality of detectors, and may estimate bio-information based on a light quantity resulting from the correction.

Example embodiments can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a physical medium storing data from a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments for example embodiments can be easily deduced by computer programmers of ordinary skill in the art, to which the disclosure pertains.

Example embodiments have been described herein. However, it will be obvious to those skilled in the art that various changes and modifications can be made without changing technical ideas and essential features of the present disclosure. Thus, it is clear that the above-described embodiments are illustrative in all aspects and are not intended to limit the scope of the present disclosure.

What is claimed is:

1. An apparatus for estimating antioxidant levels, the apparatus comprising:
   a sensor including one or more light sources configured to emit light to an object and a plurality of detectors configured to detect light reflected from the object; and
   a processor configured to transform a plurality of light quantities obtained from respective detectors of the plurality of detectors to a distance domain, the processor is further configured to combine the plurality of transformed light quantities in the distance domain into a combined light quantity, to correct the combined light quantity based on a reference light quantity, wherein the reference light quantity corrects for a deviation of a distance between the one or more light sources and the plurality of detectors to provide a corrected light quantity, and to estimate an antioxidant level based on the corrected light quantity,
   wherein the processor corrects the combined light quantity based on a difference between the reference light quantity and the combined light quantity,
   wherein the processor is further configured to drive the one or more light sources to emit light to a reflector, to obtain a plurality of light quantities from respective detectors of the plurality of detectors, to transform the plurality of light quantities to the distance domain, and to generate the reference light quantity by combining the plurality of transformed light quantities in the distance domain,
   wherein the processor is further configured to calculate absorbance by applying a logarithmic operation to the difference between the reference light quantity and the combined light quantity, to obtain an antioxidant peak by combining the calculated absorbance, and to estimate the antioxidant level by applying the obtained antioxidant peak to a predefined antioxidant level estimation model.

2. The apparatus of claim 1, wherein the processor transforms the plurality of light quantities to the distance domain by applying a logarithmic operation to each of the plurality of light quantities.

3. The apparatus of claim 1, wherein the processor combines the plurality of transformed light quantities using at least one of an arithmetic mean, a harmonic mean, and a geometric mean in the distance domain.

4. The apparatus of claim 1, wherein the one or more light sources have a wavelength range of 400 nm to 600 nm.

5. The apparatus of claim 1, wherein the processor simultaneously drives all or some of the one or more light sources or sequentially drives the one or more light sources according to wavelength.

6. The apparatus of claim 1, wherein the plurality of detectors are at least four in number.

7. A method of estimating antioxidant levels, the method comprising:
   using one or more light sources to emit light to an object;
   using a plurality of detectors to detect light reflected from the object;
   using a processor to: transform a plurality of light quantities obtained from respective detectors of the plurality of detectors to a distance domain;
   combine the transformed plurality of light quantities in the distance domain to provide a combined light quantity;
   correct the combined light quantity based on a reference light quantity, wherein the reference light quantity corrects for a deviation of a distance between the one or more light sources and the plurality of detectors; and
   estimate an antioxidant level based on the corrected light quantity,
   wherein the correcting of the combined light quantity comprises correcting the combined light quantity based on a difference between the reference light quantity and the combined light quantity,
   wherein the reference light quantity is generated by driving the one or more light sources to emit light to a reflector, obtaining a plurality of light quantities from respective detectors of the plurality of detectors, transforming the plurality of light quantities to the distance domain, and combining the plurality of transformed light quantities in the distance domain,
   wherein the estimating an antioxidant level comprises
   calculating absorbance by applying a logarithmic operation to the difference between the reference light quantity and the combined light quantity, obtaining an antioxidant peak by combining the calculated absorbance, and estimating the antioxidant level by applying the obtained antioxidant peak to a predefined antioxidant level estimation model.

8. The method of claim 7, wherein the transforming the plurality of light quantities to the distance domain comprises using the processor to apply a logarithmic operation to each of the plurality of light quantities.

9. The method of claim 7, wherein the combining the plurality of the transformed light quantities in the distance domain comprises determining at least one of an arithmetic mean, a harmonic mean, and a geometric mean.

10. An electronic device comprising:
    a main body;
    a sensor including one or more light sources and a plurality of detectors which are disposed on a first surface of the main body;
    a display device disposed on a second surface of the main body; and a processor configured to drive the one or more light sources, to transform a plurality of light quantities obtained from respective detectors of the plurality of detectors to a distance domain, to combine the plurality of transformed light quantities in the distance domain to provide a combined light quantity, to correct the combined light quantity based on a reference light quantity to provide a corrected light quantity, the reference light quantity correcting for a deviation of a distance between the one or more light sources and the plurality of detectors, and to estimate an antioxidant level based on the corrected light quantity, wherein the processor corrects the combined light quantity based on a difference between the reference light quantity and the combined light quantity, wherein the processor is further configured to drive the one or more light sources to emit light to a reflector, to obtain a plurality of light quantities from respective detectors of the plurality of detectors, to transform the plurality of light quantities to the distance domain, and to generate the reference light quantity by combining the plurality of transformed light quantities in the distance domain, wherein the processor is further configured to calculate absorbance by applying a logarithmic operation to the difference between the reference light quantity and the combined light quantity, to obtain an antioxidant peak by combining the calculated absorbance, and to estimate the antioxidant level by applying the obtained antioxidant peak to a predefined antioxidant level estimation model, wherein during estimation of the antioxidant level, the processor outputs a text message for guiding a user to estimate the antioxidant level, and upon completing the estimation of the antioxidant level, the processor outputs an estimation result to the display device.

* * * * *